United States Patent [19]

Younes

[11] Patent Number: 5,044,362

[45] Date of Patent: Sep. 3, 1991

[54] LUNG VENTILATOR DEVICE

[75] Inventor: Magdy Younes, Winnipeg, Canada

[73] Assignee: University of Manitoba, Winnipag, Canada

[21] Appl. No.: 496,172

[22] Filed: Mar. 20, 1990

Related U.S. Application Data

[63] Continuation of Ser. No. 158,752, Feb. 22, 1988, abandoned.

[30] Foreign Application Priority Data

Feb. 21, 1987 [GB] United Kingdom ................. 8704104

[51] Int. Cl.$^5$ .............................................. A61M 16/00
[52] U.S. Cl. ........................... 128/204.21; 128/204.23; 128/205.18
[58] Field of Search ...................... 128/204.18, 204.21, 128/204.23, 204.26, 205.18

[56] References Cited

U.S. PATENT DOCUMENTS

| 1,406,141 | 2/1922 | Anston ............................ | 128/205.18 |
| 4,036,221 | 7/1977 | Hillsman et al. ................ | 128/204.23 |
| 4,121,578 | 10/1978 | Torzala ........................... | 128/204.23 |
| 4,459,982 | 7/1984 | Fry ................................... | 128/204.23 |
| 4,587,967 | 5/1986 | Chu et al. ........................ | 128/205.18 |
| 4,617,637 | 10/1986 | Chu et al. ............................ | 364/505 |
| 4,726,366 | 2/1988 | Apple et al. ..................... | 128/205.18 |

FOREIGN PATENT DOCUMENTS

| 3306607 | 9/1983 | Fed. Rep. of Germany . |
| 2328452 | 10/1976 | France . |
| 1541852 | 3/1979 | United Kingdom . |
| 2054387 | 2/1981 | United Kingdom . |
| 2121292 | 12/1983 | United Kingdom . |

Primary Examiner—Aaron J. Lewis
Attorney, Agent, or Firm—Sim & McBurney

[57] ABSTRACT

A novel ventilating apparatus for the delivery of air or a desired gas mixture to a patient by displacement of an electric motor actuated piston in a chamber to expel such gas while electronic control ensures that the force applied to the piston is of a pattern and magnitude. In one preferred embodiment, the ventilating apparatus provides a proportional assist to the breathing pattern of the patient.

15 Claims, 2 Drawing Sheets

LUNG VENTILATOR DEVICE

This is a continuation of application Ser. No. 158,752, filed Feb. 22, 1988, now abandoned.

FIELD OF INVENTION

The present invention relates to a ventilator device to assist in ventilating the lungs of a patient in proportion to a desired function.

BACKGROUND TO THE INVENTION

Positive pressure ventilators are devices which are used to force gases, usually air or oxygen-enriched air, into the lungs of patients who, for one reason or another, are incapable of sustaining adequate ventilation entirely through their own efforts. The source of pressure may be a piston device, a built in blower or a high pressure line Commercially-available ventilators utilize various mechanisms to regulate the pressure applied to the patient's airway. In all cases, a breath is triggered which sets in motion a sequence of events during which pressure is applied until a volume or pressure target is reached, at which time the pressure cycle ends. Once the cycle is triggered, the ventilator proceeds in a predetermined manner, set by adjustments of dials on the control panel of the unit. With such devices, the patient has no control over the maximum pressure or the tidal volume received during the cycle. The only control the patient has is in the triggering step since some commercial ventilators have a mode in which the patient can trigger the cycle (assist/control).

I am aware of prior art proposals to effect modifications to commercially-available pressure-powered ventilators to allow the pressure produced to vary with electrical activity recorded from a respiratory nerve (see Remmers et al, "Servo Respirator Constructed from a Positive-Pressure Ventilator", J. Appl. Physiol. 41: 252 to 255, 1976) or with flow (see Poon et al, "A Device to Provide Respiratory Mechanical Unloading", IEEE Trans. Biomed. Eng. 33: 361 to 365, 1986). Such modifications can be implemented only in pressure-powered devices.

Some known prior art patents describe a variety of breathing devices. U.S. Pat. No. 3,985,124 describes a spirometer for measurement of the rate and volume of expiratory breathing to create a graphic record of the same. This device possesses an expansible chamber of the piston type which expands in proportion to the exhaled air.

U.S. Pat. No. 3,669,097 describes a device for increasing the capacity and strength of lungs. An expansible bellows chamber is connected to a conduit having a mouthpiece. A selectively-adjustable valve is present in the conduit for constricting the passage from the mouthpiece to the inlet to the bellows chamber, so that a force in excess of the normal pressure developed by the lungs is required to expand the bellows.

U.S. Pat. No. 4,301,810 describes a ventilatory muscle training apparatus comprising a reservoir and a mouthpiece and also having a simple valving system to vent stale air from the reservoir during exhalation and let fresh air into the reservoir during inhalation. The air flow through the mouthpiece is monitored to ensure the intended manner of use of the apparatus is maintained.

U.S. Pat. No. 4,462,410 describes a recording spirometer for performing a breath test which uses a movable pusher plate which is moved in response to the breathing of the patient and a recording medium which enables a record to be made of the volume of air expelled by a patient as a function of time.

U.S. Pat. No. 4,487,207 describes a lung exercise device which has a mouthpiece through which a patient inhales. A conduit connects the conduit to an air inlet and a valve is located in the conduit, normally biased to a closed position. Upon inhaling, the valve is opened and the amount of air inhaled is monitored.

SUMMARY OF INVENTION

In accordance with the present invention, there is provided a novel type of lung ventilator apparatus which exhibits considerable versatility not exhibited by prior art ventilating devices with a relatively simple electrically-powered operation. In the present invention, the gas pressure at the patient's airway is determined by the action of an electric motor pushing or pulling on a piston reciprocating in a chamber in relation to any desired command input. The electrical motor moves the piston with a force proportional to magnitude of the power applied to the motor.

The electronic circuitry provides electrical power to the device motor sufficient to generate a force on the piston and hence gases in the chamber of any desired pattern and magnitude. The electric motor responds to the instantaneous difference between a desired output and the actual output.

The desired condition may be determined by the ongoing performance of the patient in the inspiration and respiration of gases, such as the inspired gas volume or gas flow. In this manner, the ventilation device delivers an assist in proportion to the patient's own effort. Alternatively, the desired condition may be a preset external function, or a combination of on-going performance and external function.

The lung ventilating apparatus of the invention represents a novel ventilator design and construction which can effect ventilation of patients, not only in the same manner and modalities as provided by current ventilators but also includes provision for a different form of ventilatory assist, namely a proportional assist.

The difference between the latter and other modalities is that the patient has total control over his breathing pattern. In this modality, the apparatus works on the principle of positive feedback, namely the more volume the patient takes, the more pressure the machine provides. The adjustable parameter is not a target pressure or a target volume, but a degree of assist (or proportionality) to the patient's breathing pattern. Thus, if the patient's respiratory system is such that it requires 40 cmH$_2$O per liter of inflation, the machine adjusts to provide a specified amount of pressure/unit of inhaled air. If in this case, the proportionality is set to 20 cmH$_2$O/l, the patient has to do half the work and the machine does the other half, and so on. There is no requirement that the patient take in a certain volume or reach a certain pressure. As soon as the patient decreases his own effort, air stops going in and the machine stops pumping.

There are several advantages to this type of assist (i.e. proportional assist), as follows:
1) There is much less risk of overinflation with its complications (barotrauma);
2) Because the machine pumps in perfect synchrony with patient's effort, there is no "fighting" between patient and respirator which occurs with conventional machines when the patient wants to exhale, for example, while the machine continues to pump because a predetermined target has not been reached. With the proportional assist provided by the device of the invention, there is a decreased need for sedation to suppress the fighting. The patient is more vigorous, with a resulting salutary effect on the body's defense mechanisms.

3) Because the patient is doing part of the work, there is no potential for disuse atrophy of his respiratory muscles. This is a serious problem with current ventilators and results in difficulties at the time of weaning.

4) For the same reasons as given in (2) and (3) above (no fighting and patient doing part of the work), the peak pressure required at the airway to result in a given ventilation is considerably less, resulting in the possibility to ventilate the patient through nasal or face masks thereby avoiding intubation altogether. The risk of infection, and level of discomfort, are decreased as a result. Respiratory infection is almost invariable following intubation, and is a common cause of death in critically ill, ventilated patients.

Although the ventilating apparatus of the invention was designed specifically for the purpose of delivering this volume proportional assist mode, the design principles used to accomplish this end also make it possible to use the machine, with very minor electronic additions, to deliver pressure in proportion to any desired input. This extreme versatility permits adaptations to fit future needs with minimal modification.

DESCRIPTION OF PREFERRED EMBODIMENT

Figure 3:
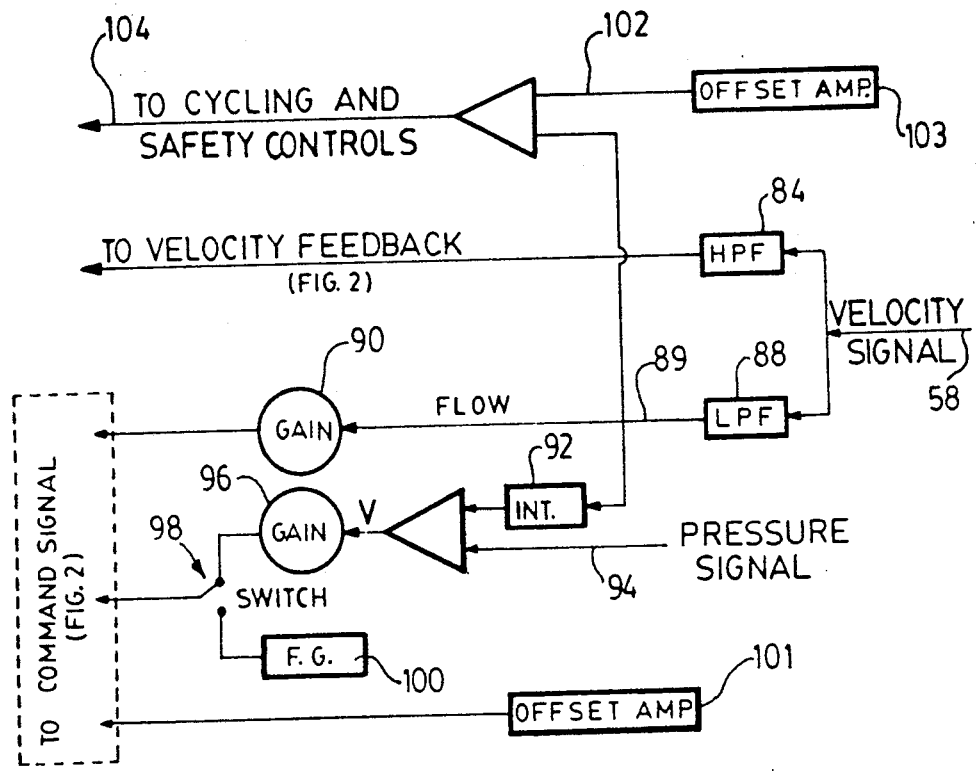
FIG. 3 is a schematic representation of the various command signals for the electronic circuitry of FIG. 2.
Figure 1:
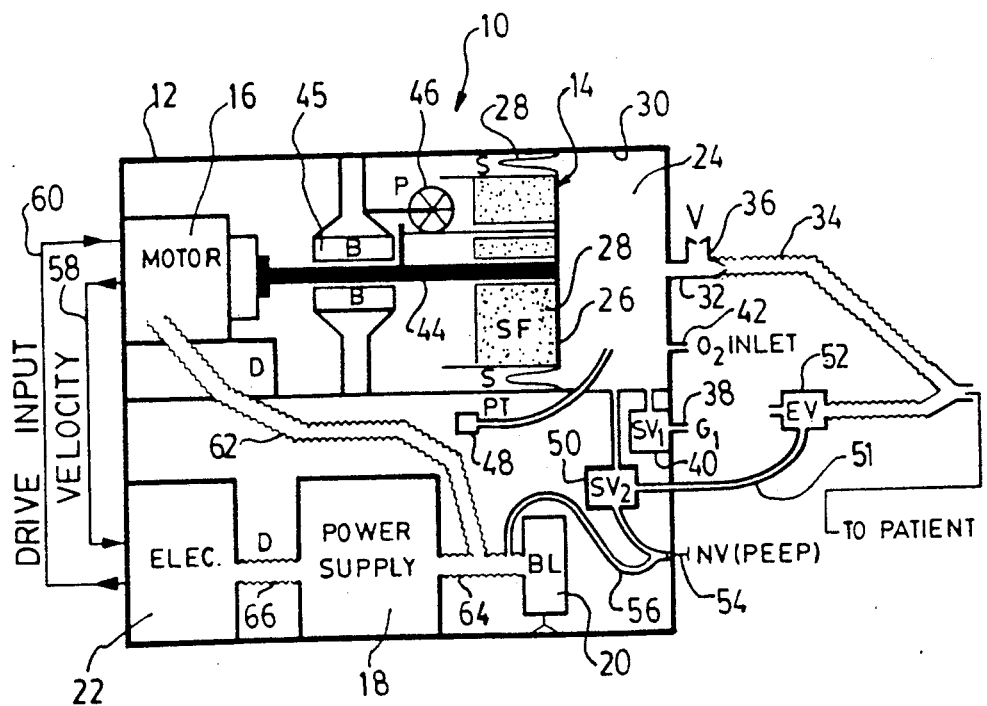
FIG. 1 is a schematic representation of a lung ventilator device provided in accordance with one embodiment of the invention.

Referring to the drawings, a lung ventilating apparatus 10 comprises a plurality of components housed in housing 12. The components located in the housing 12 comprise a piston head 14, a drive motor 16 for the piston 14, an electrical power supply 18 for the unit 10, an air blower 20 and electronic controls 22.

The piston head 14 is mounted for reciprocal movement in the housing 12 to provide a chamber 24 of variable volume depending on the position of the piston head 14. The cross-sectional area of the piston head 14 as well as the maximum distance of reciprocation determine the range of ventilation for which the unit 10 may be used. The choice of partition of volume displacement between these components largely depends on the power of the motor 16 to be used. For a given volume displacement, a smaller piston cross-sectional area decreases the maximum motor force required and increases the maximum required displacement and vice versa. For adult ventilation, the maximum piston displacement should be at least 3 liters while for newborn infants, a maximum displacement of 0.5 liters would suffice.

For best patient response, the piston head 14 should move with little inertia and frictional resistance. For this purpose, a light plastic material may be employed, or, as illustrated, an aluminum shell 26 with a foamed polymer reinforcement, such as, Styrofoam. Frictional resistance to piston movement may be decreased by using high quality bearings and low resistance seals, such as a rolling seal 28 between the piston head 14 and the interior chamber wall 30.

The chamber 24 is provided with an inlet/outlet opening 32 which is arranged to be joined by a flexible air pipe 34 to the airway of a patient. A one-way valve 36 communicates with the pipe 34, to allow ambient gas, usually air, to enter the piston chamber 24 through the inlet/outlet opening 32 during the exhalatory phase of the respiratory cycle, as described in more detail below.

The chamber 24 is illustrated as possessing an additional gas inlet 38 controlled by a solenoid valve 40 to permit the optional introduction of selected gas mixtures, if desired, to the chamber 24. The solenoid valve 40 is opened during expiration as the piston head 14 reciprocates to its baseline position. Alternatively, the oxygen content of the inspired gas may be enriched by admitting a continuous flow of oxygen into the chamber 24 through an optional gas inlet 42.

The piston head 14 is mounted on a piston rod 44 for reciprocation of the piston head 14 for the purpose of alternatively decreasing and increasing the volume of the cylinder 24. The piston rod 46 is mounted in sliding relation to a suitable bearing 45. A position sensing device 46, in the form of a potentiometer, is mounted on the piston rod 44 to provide an electrical signal corresponding to the position of the piston head 14.

A pressure transducer 48 is operatively connected to the piston chamber 24 to determine the pressure in the chamber 24 which, in turn, determines the force output required by motor 16, as explained in more detail below.

The piston chamber 24 also is connected to a three-way solenoid valve 50. The solenoid valve 50 is connected via tube 51 to an expiratory valve 52 connected by flexible tubing 54 to the patient airway. During the inspiratory phase of operation of the piston 14, the solenoid valve 50 connects the chamber 24 to the expiratory valve 52, shutting it off. During the expiratory phase of operation of the piston 14, the solenoid valve 50 connects the expiratory valve 52 to a variable pressure in order to set the level of positive end-expiratory pressure (PEEP), as described in more detail below. The variable pressure is produced by controlling the resistance of a needle valve 54 mounted into the pipe 56 connecting the solenoid valve 50 to the blower 20.

The motor 16 is of the type which possesses a moving part, such as a shaft or coil, to exert a force in a forward (positive) or backward (negative) direction in proportion to the power applied to the motor 16. The maximum force requirement of the motor is determined by the area (A) of the piston head and the maximum pressure range (Pmax) for which the unit 10 is built. The equation to calculate the required force is:

$$F(kg) = \frac{Pmax(cm\ H_2O) \times A(cm^2)}{1000}$$

Hence, for example, for a piston of area 200 cm$^2$ and maximum pressure range 50 cm H$_2$O, the motor 16 should be able to generate up to 10 kg of force.

A velocity transducer 57 (FIG. 2) is mounted to the core of the motor 16 to generate a signal 58 proportional to the rate of motion of the piston head 14. This signal is used for a variety of purposes, as described below with respect to FIG. 2. The motor 16 is powered by a power line 60 from the electronic module 22 (see also FIG. 2).

The blower 20 may be connected by flexible pipes 62, 64 and 66 to the motor 16, power supply 18 and electronic module 22 respectively to provide cooling air as required. The power supply 18 provides the power requirements of the motor 16 and the electronic module 22.

The electronic module 22 functions to provide the electrical signal drive input 60 to the motor 16 to cause the motor 16 to generate a drive force to the piston 14 of a pattern and magnitude that reproduces, as closely as possible, the desired pattern and magnitude of pressure to be delivered to the patient from the chamber 24. It is preferred to employ a fast-responding motor, so that a change in drive input results in an almost instantaneous change in drive force, thereby permitting almost unlimited patterns of pressure applications.

A large variety of electronic components may be used in the electronic circuitry in conjunction with the pressure generating device (i.e. the combination of motor 16, piston head 14 and power supply 18) to produce a corresponding variety of pressure patterns, as described further below.

OPERATION

Figure 2:
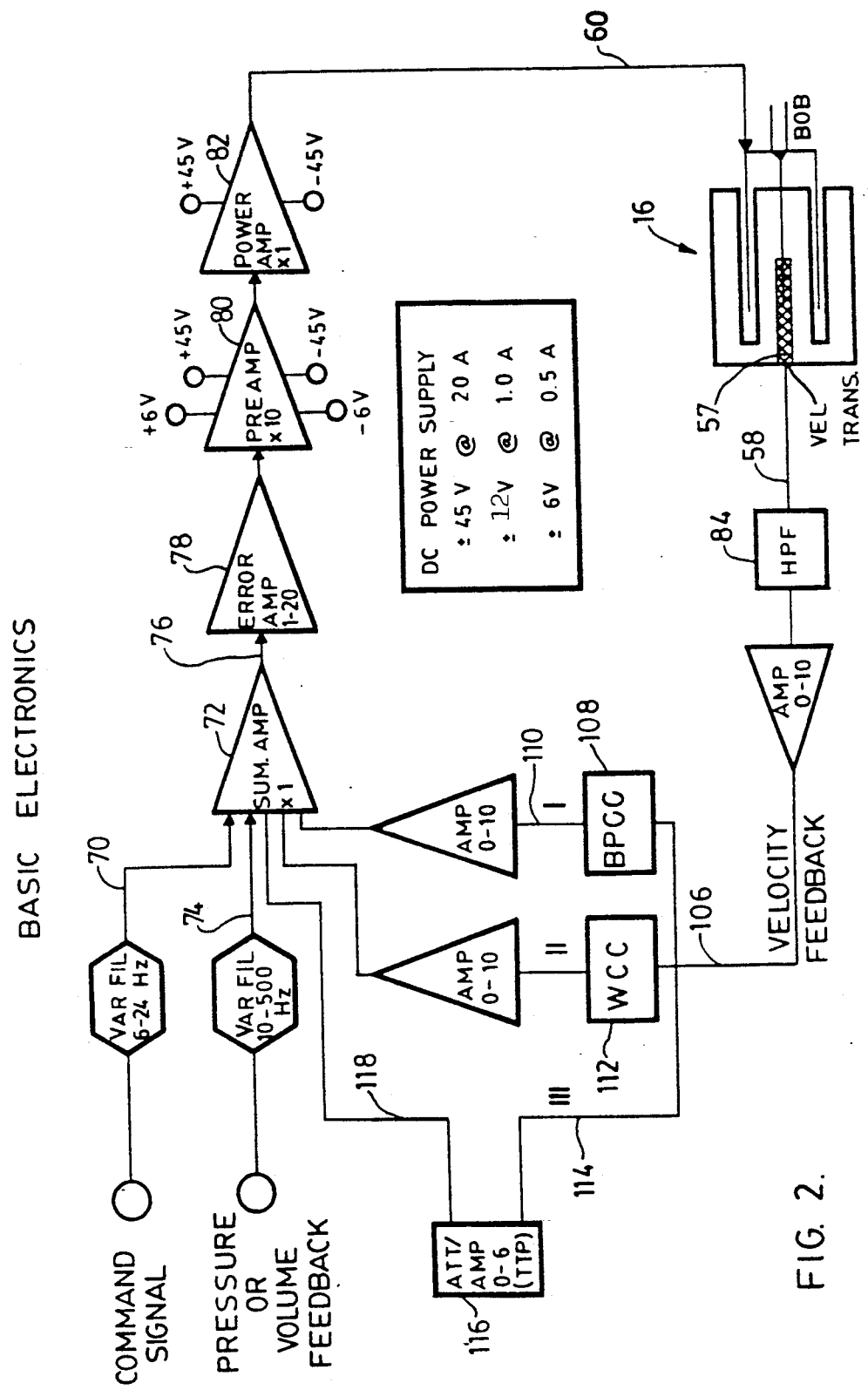
FIG. 2 is a schematic representation of the electronic circuitry used with the apparatus of FIG. 1.

The operation of the ventilating device 10 is described in conjunction with the electronic circuitry shown schematically in FIG. 2 and the command signals shown schematically in FIG. 3.

The motor 16 responds to the instantaneous difference, after suitable amplification, between a desired output, being the command signal, and the actual output. As seen in FIG. 2, the desired output is inputted by line 70 to a summing amplifier 72 to which also is fed a feedback signal (corresponding to the actual state of affairs) by line 74.

For example, if it is desired to produce a signal that is proportional to the inspired volume, the inspired volume signal is used as the command signal. The pressure in the piston chamber 24, as measured by the pressure transducer 48, is used as feedback. If the measured pressure in the chamber 24 is different from the one desired as determined by the summing amplifier 72, then an error signal is generated in line 76. The error signal, after suitable amplification by amplifiers 78, 80, then controls the output of a power amplifier 82 which provides the control signal in line 60 to the motor 16.

When the pressure in the piston chamber 24 is measured by the pressure transducer 48 as just described, the ventilator unit 10 can deliver pressure from the piston chamber 24 in proportion to inspired volume (as just described), inspired flow rate (with the flow rate used as the command signal), a combination of the two or in proportion to any other desired command signal.

For example, if a sine wave or a ramp voltage is used as the command signal, the ventilator unit produces pressure in the corresponding manner. As a result of this versatility, it is possible to employ the unit 10 as a high frequency ventilator alone or in combination with volume or flow assist.

If inspired volume is used as a feedback, the unit also delivers pressure in a pattern which causes inspired volume to follow the pattern of the command signal, thereby functioning as a volume ventilator.

In the electronic circuitry 22, the summing amplifier 72 also receives feedback from the velocity transducer 57 by line 58. This additional feedback tends to prevent rapid changes in pressure which otherwise may trigger oscillations. The output of the velocity transducer 57 reflects the motion of the piston related to air moving into the subject as well as motion related to compression or decompression of gas in the system. The former component is a relatively slow event whereas the latter component incorporates high frequency components, which are desirable as feedback to prevent oscillations. For this reason, the signal in line 58 is passed through a high pass filter 84. The filter output in line 106 is used as a velocity feedback in three arms.

One arm of the net velocity signal in line 106 is passed through a bidirectional peak clipping circuit 108, which clips the signal above and below an adjustable level. The signal so produced in line 110 is amplified and passed to the summing amplifier 72.

A second arm of the net velocity signal in line 106 is passed through a window clipping circuit 112, which passes only that part of the signal above or below an adjustable level and is designed to abort massive oscillations in the event of failure of other feedback. The level above or below which net velocity signal is passed is adjusted to be above the signal level associated with response to the control signal.

The third arm, in line 114, containing the entire net velocity signal, is passed through an adjustable attenuator with the resulting signal passing by line 118 to the summing amplifier 72. With the two clipping circuits 108 and 112 in place, the gain on the main velocity signal in line 114 need only be small.

Generally, switches permit the operator to select the function or combination of functions to be channeled to the summing amplifier 72 and variable gain controls permit selection of the magnitude of the assist. The various functions available for the illustrated embodiment are shown schematically in FIG. 3 and will now be described:

(a) Inspired flow: When the high frequency components of the output of the velocity transducer 57 in line 58 are filtered out, the remaining signal agrees very well with flow measured independently at the airway 34. Accordingly, the velocity signal in line 58 is passed through a low pass filter 88 and the resulting signal 89 is used as a command signal in line 70 for the ventilator unit 10 to produce pressure in proportion to inspired flow (i.e. resistive assist). A gain control 90 permits the selection of the magnitude of the assist. In practice, the flow signal is permanently connected to the summing amplifier 72 by line 70 and a minimum gain is dialed to offset the resistance of the tubing. When a greater assist is required to offset the patient's own resistance, the gain is increased.

(b) Inspired volume: The signal related to inspired flow (line 89) may be integrated in integrator 92 to provide inspired volume. A signal proportional to pressure (line 94) is subtracted to allow for piston chamber compression. The magnitude of the pressure signal to be subtracted is a function of the gas volume of the system, according to Boyle's law. When the resulting signal is routed to the summing amplifier 72 by line 70, the ventilator unit 10 develops pressure in proportion to inspired volume. The magnitude of the assist obtained again may be controlled by a gain device 96.

(c) Ramp generator: This mode of operation permits the ventilator unit 10 to function independent of patient effort and provides a controlled ventilation. This function can be activated by the operator by throwing switch 98 to bring the function generator 100 into the circuit Alternatively, provision may be made for the ramp generator to be routed automatically to the summing amplifier 72 in the event of the failure of the patient to breathe spontaneously for a specified period of time (not shown).

(d) D.C. output: An adjustable DC output provided by an offset amplifier 101 also is routed to the summing amplifier 72, to result in the generation of continuous pressure.

The electronic circuitry 22 also includes cycling controls (not shown) to take into account that air is exchanged between patient and ventilator unit 10 only during the inspiration phase of the respiratory cycle and it is necessary to reset various controls in the "off" phase in preparation for the next cycle. These controls also effect closure of the expiratory valve 52 during the pumping phase.

During inspiration, air moves from the piston chamber 24 to the patient via tube 34 under the influence of the pressure produced by the moving piston head 14. During expiration, air escapes by the expiratory valve 52 while the one-way valve 36 prevents expired air from re-entering the chamber 24.

At the commencement of inspiration, the piston head 14 begins to move forward in the chamber 24, either as a result of the patient pulling in (assist mode) or as a result of the piston pushing (in response to a ramp command in the controlled mode). This forward motion then generates a flow signal which, when it exceeds a predetermined level, causes the expiratory valve 52 to close to ensure that pressure is conveyed to the patient. This result is achieved by summing the flow signal in line 89 with a DC offset voltage in line 102 from offset amplifier 103 and passing the summed signal in line 104 through a zero crossing detection circuit.

The level of the offset voltage 102 may be varied and usually is kept slightly above zero. Once the flow exceeds this minimal level, a square voltage output is generated which activates valve 50, thereby connecting the chamber 24 to the valve 52 and closing the latter. Flow then continues into the patient as long as patient effort plus pressure output by the ventilator unit 10 exceed the elastic recoil of the respiratory system. When patient effort declines at the end of the patient's spontaneous inspiration, inspiratory flow ceases.

As the flow signal crosses the offset level on its return to zero at the end of the inspiratory cycle, the valve 50 is inactivated, so releasing the pressure in the expiratory valve 54 and allowing the patient to exhale. In the case of volume assist, the flow integrator is set to zero, thereby removing the positive command signal from the summing amplifier 72. In the case of controlled ventilation, the end of the inspiration takes place at the end of the ramp voltage, at which time the ramp generator resets its own output to zero.

At the same time, a negative voltage is gated to the summing amplifier 72, which causes the piston head 14 to pull back allowing air to enter the chamber 24 through the one-way valve 36, if air is the desired gas. If desired, the solenoid valve 40 may be opened at the same time to permit pressurized gas of a specific composition to be admitted. The piston head 14 retracts until the piston position, as indicated by the output of the potentiometer 46, reaches a preset level.

When this condition is reached, the negative voltage to the summing amplifier 72 is interrupted and the solenoid valve 40 is closed. The active command signal is the output of the offset amplifier. The pressure in the piston chamber 24 remains at this level throughout the remainder of the expiratory phase and until the beginning of the next inspiratory phase. The output of the offset amplifier is normally set just below its PEEP level, so that the patient need only exert minimal effort to get the piston head 14 moving at the beginning of inspiration.

The electronic circuitry 22 may include safety features powered by battery in the event of power failure. For example, an alarm may be made to sound in the event that there is a power failure, a failure of pressure to cycle for a preset period, an excess pressure or a large inspired volume.

A variety of gauges, read-outs and recorders may be provided to display, store or compilate a variety of parameters, including breath by breath or moving averages, of tidal volume, ventilation frequency, inspiratory duration, duty cycle (inspiratory duration/cycle duration) and respiratory system compliance.

SUMMARY OF DISCLOSURE

In summary of this disclosure, the present invention provides a novel ventilation unit which is able to deliver air to a patient in accordance with a desired pattern and magnitude and which continuously monitors and maintains the desired set of conditions. Modifications are possible within the scope of this invention.

What I claim is:

1. A lung ventilator apparatus, comprising:
   chamber means having a piston movable therein permitting the free flow of gas from said chamber means to a patient in response to a pressure gradient generated by the patient,
   electrical motor means operatively connected to said piston to apply to said piston a force which is proportional to the magnitude of the power applied thereto; and
   electronic circuit means for providing electrical power to said electrical motor means, said electronic circuit means including:
   means for generating electrical signal corresponding to the inspired flow rate and the inspired flow volume, respectively, of said gas from said chamber means to said patient,
   means for varying the proportionality for each of said electrical signals, and
   means for generating an electrical signal to apply electrical power to said electrical motor means in proportion to the sum of said inspired flow rate and said inspired flow volume signals,
   whereby said piston provides an assist to the patient's breathing function in said proportion.

2. The apparatus of claim 1 wherein an outlet from said chamber for said gas is connected through valve means to a breathing tube intended for delivery of said gas to the airway of a patient, said valve means permitting gases from said chamber means to enter said breathing tube during inhalation by said patient and permitting gases to enter said chamber during exhalation by said patient.

3. The apparatus of claim 2 wherein said chamber also has an inlet for receiving a continuous flow of oxygen or other gas.

4. The apparatus of claim 2 wherein said chamber also has a valved inlet for selectively receiving a gas therein during exhalation by said patient.

5. The apparatus of claim 2 wherein said breathing tube also is connected to an exhalation tube having a valve therein which is selectively operable to permit gases to pass from the patient out of said exhalation tube during exhalation by said patient and to prevent gases from passing through said exhalation tube during inhalation by said patient.

6. The apparatus of claim 5 wherein said selectively-operable valve in said exhalation tube is pneumatically connected to said chamber means to be opened and closed in response to the direction of movement of said piston in said chamber means.

7. The apparatus of claim 1 including pressure transducer means operatively connected to said chamber means for detecting the pressure therein and for generating an electrical signal proportional to the magnitude of the detected pressure.

8. A lung ventilator apparatus, comprising:
chamber means having a piston movable therein permitting the free flow of gas from said chamber means to a patient in response to a pressure gradient generated by the patient,
pressure transducer means operatively connected to said chamber means for detecting the pressure therein and for generating an electrical signal proportional to the magnitude of the detected pressure,
electrical motor means operatively connected to said piston to apply to said piston a force which is proportional to the magnitude of the power applied thereto, and
electronic circuit means for providing electrical power to said electrical motor means,
said electronic circuit means including:
means for generating electrical signals corresponding to the inspired flow rate and the inspired flow volume, respectively, of said gas from said chamber means to said patient,
means for varying the proportionality for each of said signals,
means for generating an electrical signal to apply electrical power to said electrical motor means in proportion to the sum of said inspired flow rate and inspired flow of flow signals,
comparator means for continuously comparing the magnitude of said detected pressure signal during inhalation by said patient with the expected pressure signal corresponding to the applied electrical power to said electrical motor means and for generating a comparator electrical signal corresponding in magnitude to any detected difference between said detected pressure signal and said expected pressure signal, and
control signal generating means for generating an electrical signal to said electrical motor means in response to said comparator electrical signal to move said piston with a force corresponding to the magnitude of said electrical signal.

9. The apparatus of claim 8 wherein said motor means includes velocity transducer means associated with said motor means for generating an electrical signal proportional in magnitude to the speed of said motor and including high pass filter means fed by said electrical signal generated by said velocity transducer means and generating an electrical signal which is fed to said comparator means as an oscillation smoothing control signal.

10. The apparatus of claim 8 wherein said motor means includes velocity transducer means associated with said motor means for generating an electrical signal proportional in magnitude to the speed of said motor and including low pass filter means fed by said electrical signal generated by said velocity transducer means for filtering high frequency components from said electrical signal and providing a control signal of a magnitude corresponding to inspired gas flow.

11. The apparatus of claim 10 wherein said control flow signal is integrated to provide an electrical signal corresponding to inspired volume.

12. The apparatus of claim 1 wherein said electronic circuit means includes comparator means for continuously comparing the magnitude of a pressure output signal of said motor means with a desired pressure output signal of said motor means corresponding to the applied electrical power to said motor means and for generating a command signal to said motor means of a magnitude corresponding to said desired pressure output.

13. The apparatus of claim 1 wherein said electronic circuit means includes piston location detection means for detecting the position of said piston in said chamber means and for controlling said electrical motor means to move said piston in said chamber in response to said detected position.

14. A lung ventilator apparatus, comprising:
chamber means having a piston reciprocally movable therein permitting the free flow of gas from said chamber means to a patient in response to a pressure gradient generated by the patient,
said chamber means having an outlet therefrom for said gas connected through first valve means to a breathing tube having an inhalation tube portion intended to deliver said gas to the airway of a patient and an exhalation tube portion intended to pass exhaled gases from the airway of a patient to ambient atmosphere, said first valve means permitting gases from said chamber means to enter said breathing tube portion during inhalation by said patient and permitting gases to enter said chamber but not said inhalation tube portion during exhalation by said patient,
said exhalation tube portion having second valve means therein selectively operable to permit said exhaled gases from the patient to pass through the exhalation tube portion to ambient atmosphere during exhalation by said patient and to prevent gases from passing through said exhalation tube portion to ambient atmosphere during inhalation by said patient,
actuation means for said second valve means operably connected to said second valve means and said chamber means so as to cause said second valve means to be opened to permit said exhaled gases to pass to atmosphere when the patient exhales and to cause said second valve means to be closed when the patient inhales,
electrical motor means operatively connected to said piston to apply to said piston a force which is proportional to the magnitude of the power applied thereto, and
electronic circuit means for providing electrical power to said electrical motor means, said electronic circuit means including:
means for generating electrical signals corresponding to the inspired flow rate and the inspired flow volume, respectively, of said gas through said inhalation tube portion to said patient,
means for varying the proportionality for each of said signals, and means for generating an electrical signal to apply electrical power to said electrical motor means in proportion to the sum of said inspired flow rate and said inspired flow volume signals.

15. The apparatus of claim 14, wherein said actuation means for said second valve means includes means to control residual exhaled pressure at which said second valve means closes.

* * * * *